Figure 1:
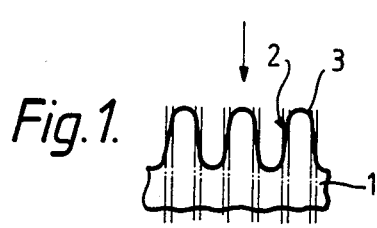

United States Patent [19]

Hood

[11] Patent Number: 4,545,082
[45] Date of Patent: Oct. 8, 1985

[54] VASCULAR PROSTHESIS

[75] Inventor: Robert G. Hood, Paisley, Scotland

[73] Assignee: Vascutek Limited, Ayr, Scotland

[21] Appl. No.: 561,590

[22] PCT Filed: Mar. 24, 1983

[86] PCT No.: PCT/GB83/00088
§ 371 Date: Nov. 25, 1983
§ 102(e) Date: Nov. 25, 1983

[87] PCT Pub. No.: WO83/03347
PCT Pub. Date: Oct. 13, 1983

[30] Foreign Application Priority Data

Mar. 25, 1982 [GB] United Kingdom ............ 8208852

[51] Int. Cl.⁴ .......................... A61F 1/24; A61F 1/00
[52] U.S. Cl. .................................. 623/1; 128/334 R; 623/12
[58] Field of Search ................. 3/1.4, 1; 128/334 R

[56] References Cited

U.S. PATENT DOCUMENTS 3,805,301 4/1974 Liebig ...................................... 3/1.4
4,047,252 9/1977 Liebig et al. ............................ 3/1.4
4,193,137 3/1980 Heck ....................................... 3/1.4

FOREIGN PATENT DOCUMENTS 860761 9/1981 U.S.S.R. ................................ 3/1.4

OTHER PUBLICATIONS

"A Method to Prevent Torsion of Arterial Prosthetic Grafts" by Robert P. Belin et al, The Journal of Thoracic & Cardiovascular Surgery, vol. 54, No. 1, Jul. 1967, p. 49.

Primary Examiner—Ronald L. Frinks
Attorney, Agent, or Firm—Larson & Taylor

[57] ABSTRACT

A vascular prosthesis intended to act as a substitute blood vessel comprises a porous corrugated tube (1) of textile material presenting a pattern of a series of axially disposed markings (3,4 or 5) on the corrugations (2) so disposed that the appearance of the pattern changes when the prosthesis is extended. The change in the appearance of the pattern as the tube is extended provides an indication to the user when the prosthesis has been extended to the desirable extent.

5 Claims, 9 Drawing Figures

VASCULAR PROSTHESIS

The subject of this invention is a vascular prosthesis of the type comprising a porous tube made of textile material formed with circumferential corrugations intended to act as a substitute blood vessel in a human or an animal body.

In placing a vascular prosthesis in position in a human or animal body it is extremely desirable that the graft should not be twisted. To this end it is known to provide on the graft at least one line of contrasting colour so that any twist in the graft becomes readily apparent. However, there is another consideration relating to the fitting of a graft. That is that the amount by which the graft is extended axially beyond its unstressed condition should be maintained within a predetermined limit. If the graft is not stretched far enough there may be an increased resistance presented to the flow of blood through the graft because of interference presented by the corrugations. If the graft is stretched too much the pores may be extended to a point where there is a danger of haemorrhage occurring at the junction between the graft and the host tissue before there has been time for the build up of tissue on the walls of the graft or the sutures at the junction may be pulled out of the host tissue if excessive stretch as a result of excessive tension in the graft itself.

It is an object of the present invention to provide an indicating means on the graft which will indicate to the surgeon who is implanting the graft not only whether the graft is straight but also when the correct amount of extension has been attained.

A vascular prosthesis according to the invention comprises a corrugated tube of textile material characterized by presenting a pattern of a series of separate axially disposed markings on the corrugations, the disposition of the markings being such that when the prosthesis is extended to about the predetermined correct degree of extension whereby to increase the angle between opposite sides of each corrugation the observed pattern of markings along the prosthesis changes to provide a signal that the correct degree of extension has been attained.

In one construction, on each crest and/or in each trough, there is provided a short axial line, so disposed that when the prosthesis is extended to the predetermined proper extent the individual lines are in alignment and show gaps between adjacent lines the projected lengths of which to an observer are a readily discernible proportion of the length of each line. Preferably the proportion is a proportion of equality i.e. the lengths of the gaps appear to be the same as the lengths of the individual lines thus providing a dashed line from one end of the prosthesis to the other with the lengths of lines and spaces all equal.

Alternatively the prosthesis may be marked with spaced circumferential lines each of which forms a short arc on the surface of the prosthesis, the axial positioning and spacing of the lines being such that when the prosthesis is extended by the desirable amount the arcs when viewed from one side of the prosthesis are spaced in a predetermined relation to one another, once again preferably equi-distantly from one another.

The arcs may be so positioned that when the prosthesis is in the unstressed state the arcs appear in groups of closely spaced lines and when the prosthesis is extended to the desirable extent the radially projected lengths of the gaps between all the arcs become equal to an observer.

In a still further alternative arrangement the markings are in the form of geometrical shapes which in the unstressed state of the prosthesis have one form and when the prosthesis is extended change to another readily distinguishable geometrical shape. For example the prosthesis may bear marks which appear as diamonds or ellipses when the prosthesis is unextended and which appear as squares or circles respectively when the prosthesis is extended to the desirable extent.

Figure 2:
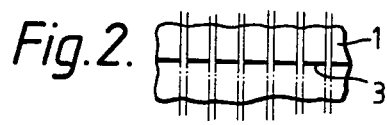
Figure 3:
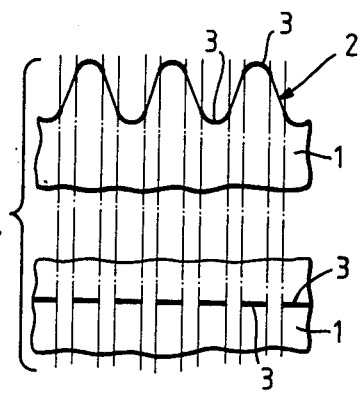

Practical embodiments of the invention are illustrated in the accompanying drawings in which FIG. 1 illustrates a vascular prosthesis in the unstressed condition indicating in side elevation the manner in which the individual axial lines are applied to the prosthesis, FIG. 2 shows how the prosthesis appears in the unextended condition looking down into the corrugations and showing the appearance of the markings and FIG. 3 shows the prosthesis of FIGS. 1 and 2 extended to the desirable amount indicating how the markings then appear.

Figure 4:
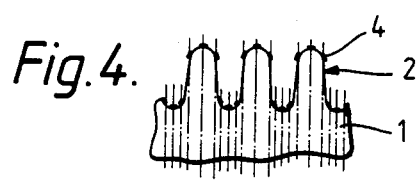
Figure 5:
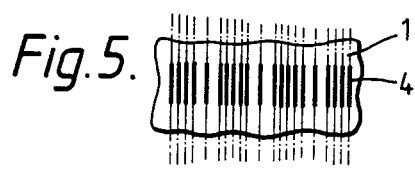
Figure 6:
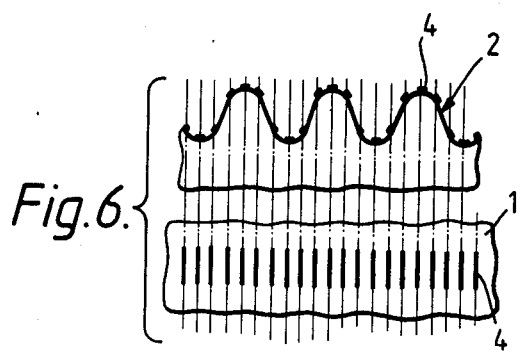

FIG. 4 illustrates a prosthesis with another form of marking in the form of arcs orientated circumferentially on the prosthesis, FIG. 5 illustrates how the prosthesis of FIG. 4 appears when looked at in the unextended condition and FIG. 6 illustrates the prosthesis of FIGS. 4 and 5 extended to the desirable amount showing the markings clearly indicating that this situation has been reached by the equal spacing of the markings.

Figure 7:
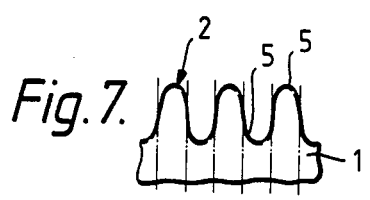
Figure 8:
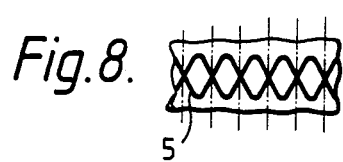
Figure 9:
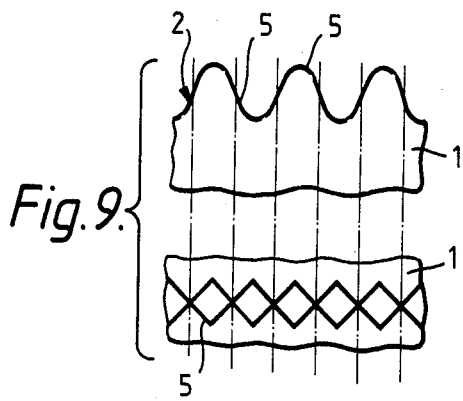

FIG. 7 illustrates a prosthesis with yet another form of marking in the form of a line of diagonally disposed square, FIG. 8 illustrates how the prosthesis appears in the unextended position looking down into the corrugations and FIG. 9 shows the prosthesis of FIGS. 7 and 8 extended to the desirable amount.

In the drawings 1 denotes the prosthesis formed with corrugations 2. In FIGS. 1, 2 and 3, the numeral 3 denotes axially orientated lines marked on the tube constituting the prosthesis while in FIGS. 4, 5 and 6, the numeral 4 denotes arcuate lines marked on the tube constituting the prosthesis. In FIGS. 7, 8 and 9 the numeral 5 indicates squares marked on the tube constituting the prosthesis.

Referring first to the construction of FIGS. 1, 2 and 3, the prosthesis appears as illustrated in FIG. 2 with the lines marked thereon indicating a more or less continuous line or at least with gaps between adjacent lines much smaller than the lengths of the lines themselves. When the prosthesis is extended to the most desirable extend for use as a graft the angle between the sides of each corrugation is increased so that the radially projected length of each line or each space as the case may be as seen by an observer is changed to show a dashed line along the length of the prosthesis in which the individual lines and spaces are of equal length.

In the construction of FIGS. 4, 5 and 6, the unextended prosthesis appears as in FIG. 5 with the lines appearing in groups in which the spacing is irregular. When the prosthesis is extended to the desirable extend for use as a graft once again the projected distance between adjacent lines is changed because of the change in angularity of the surface carrying the lines and they appear all equi-spaced in an axial direction.

In the construction of FIGS. 7, 8 and 9 the unextended prosthesis appears in FIG. 7 with the squares appearing as transversely orientated diamonds. When the prosthesis is extended to the desirable extent the diamond shapes appear as squares or quasi-squares.

I claim:

1. A vascular prosthesis which comprises a corrugated tube (1) of textile material is characterized by presenting a pattern of a series of separate axially disposed markings (3 or 4 or 5) on the corrugations (2), the disposition of the markings being such that when the prosthesis is extended to about the predetermined correct degree of extension whereby to increase the angle between opposite sides of each corrugation the observed pattern of markings along the prosthesis changes to provide a signal that the correct degree of extension has been attained.

2. A vascular prosthesis according to claim 1 characterized in that on each crest and/or in each trough of each corrugation there is provided a short axial line (3) so disposed that when the prosthesis is extended to the predetermined proper extent the individual lines are in alignment and show gaps between adjacent lines the projected lengths of which to an observer are a readily discernible proportion of the length of each line.

3. A vascular prosthesis according to claim 1 characterized in that the corrugations (2) are marked with spaced circumferential lines (4) each of which forms a short arc on the surface of the prosthesis, the axial positioning and spacing of the lines being such that when the prosthesis is extended by the desirable amount the arcs when viewed from one side of the prosthesis are spaced in a predetermined relation to one another.

4. A vascular prosthesis according to claim 1 characterized in that the markings are in the form of geometrical shapes which in the unstressed state of the prosthesis have one form and when the prosthesis is extended change to another readily distinguishable geometrical shape.

5. A vascular prosthesis according to claim 4 characterized in that the markings appear as diamonds (5) when the prosthesis is unextended and which appear as squares when the prosthesis is extended to the desirable extent.

* * * * *